US012605068B2

(12) United States Patent
Alasaarela et al.

(10) Patent No.: US 12,605,068 B2
(45) Date of Patent: Apr. 21, 2026

(54) OPHTHALMIC APPARATUS AND ALIGNMENT METHOD

(71) Applicant: Optomed Plc, Oulu (FI)

(72) Inventors: Ilkka Alasaarela, Oulu (FI); Matti Pohjoisaho, Oulu (FI)

(73) Assignee: OPTOMED PLC, Oulu (FI)

( * ) Notice: Subject to any disclaimer, the term of this patent is extended or adjusted under 35 U.S.C. 154(b) by 405 days.

(21) Appl. No.: 18/331,982

(22) Filed: Jun. 9, 2023

(65) Prior Publication Data

US 2023/0404402 A1    Dec. 21, 2023

(30) Foreign Application Priority Data

Jun. 9, 2022    (FI) ..................................... 20225505

(51) Int. Cl.
*A61B 3/15* (2006.01)
*A61B 3/12* (2006.01)

(52) U.S. Cl.
CPC ................ *A61B 3/152* (2013.01); *A61B 3/12* (2013.01)

(58) Field of Classification Search
CPC ......... A61B 3/152; A61B 3/12; A61B 3/0016; A61B 3/0041; A61B 3/0083; A61B 3/1216; A61B 3/1225

(Continued)

(56) References Cited

U.S. PATENT DOCUMENTS

2013/0135584 A1    5/2013    Alasaarela et al.
2014/0313485 A1    10/2014    Umekawa
2018/0055358 A1    3/2018    Nakajima

FOREIGN PATENT DOCUMENTS

EP    1245182 A1    10/2002
EP    1803390 A2    7/2007

(Continued)

OTHER PUBLICATIONS

Finland Search Report for FI20225505 dated Jan. 11, 2023, 2 pages.

*Primary Examiner* — William R Alexander
*Assistant Examiner* — Alaina Marie Swanson
(74) *Attorney, Agent, or Firm* — Nixon & Vanderhye PC

(57) ABSTRACT

An ophthalmic apparatus comprises an alignment arrangement, which outputs rays of alignment light of a first alignment pattern in a converging manner toward a first target plane, forms a predetermined reflection pattern of the first alignment pattern on said first target plane based on the convergence, causes the rays of the alignment light to have an alignment light waist zone that includes the first target plane based on the convergence, causes a reflection pattern of the first alignment pattern outside the first target plane to deviate from the predetermined reflection pattern based on the convergence. A communication interface of the ophthalmic apparatus outputs information on the reflection pattern of the first alignment pattern reflected from said a posterior surface of the crystalline lens of the eye when the ophthalmic apparatus is directed toward the eye for guiding and/or controlling a user based on the reflection pattern of the first alignment pattern that is varying with the position of the posterior surface of the crystalline lens on said posterior surface to find the working distance from the eye where the predetermined shape of the first alignment pattern is on said posterior surface.

11 Claims, 9 Drawing Sheets

(58) Field of Classification Search
USPC ......................................................... 351/208
See application file for complete search history.

(56)                         References Cited

FOREIGN PATENT DOCUMENTS

| EP | 1935330 A1 | * | 6/2008 | ............... A61B 3/12 |
|----|------------|---|--------|---------------------------|
| EP | 2138093 A1 | * | 12/2009 | ............. A61B 3/152 |
| JP | 2021074101 A | * | 5/2021 | |

* cited by examiner

VIEW FROM SIDE

VIEW FROM TOP

210    Wc

262

CORNEA
ALIGNEMENT
LIGHT BEAM

Z-AXIS

105

USER
40          16
60

DATA
PROCESSING          UI          10

IMAGING
ARRANGE-
MENT          14, 20

IMAGING
ARRANGE-
MENT          ALIGNMENT
ARRANGE-
MENT          104

14
22
IMAGING
ARRANGE-
MENT

30'          ALIGNMENT
ARRANGEMENT          30"
12          30

ILLUMINATION
ARRANGEMENT
18

60
500          502
PROCESSOR          MEMORY

OPHTHALMIC APPARATUS AND ALIGNMENT METHOD

CROSS-REFERENCE TO RELATED APPLICATIONS

This application claims priority to FI Patent Application No. 20225505 filed Jun. 9, 2022, the entire contents of which is hereby incorporated by reference.

FIELD

The invention relates to an ophthalmic apparatus and an alignment method.

BACKGROUND

A typical problem with ophthalmic instruments is how to align the instrument with a patient's eye. The problem is particularly difficult with examination instruments which examine optically portions of an eye behind the iris, for example such as fundus cameras, where a wrong alignment may lead to dim and/or vignetted images and/or spurious reflections. The internal structure of the eyes has a large variation and distances between the cornea and the crystalline lens, for example, may be quite different from person to person. That causes optical challenges to the ophthalmic instruments. In many cases there is no precise enough way to know if the ophthalmic instrument is correctly aligned with respect to the eye that is examined.

Hence, an improvement to the alignment would be welcome.

BRIEF DESCRIPTION

The present invention seeks to provide an improvement in the alignment.

The invention is defined by the independent claims. Embodiments are defined in the dependent claims.

If one or more of the embodiments is considered not to fall under the scope of the independent claims, such an embodiment is or such embodiments are still useful for understanding features of the invention.

LIST OF DRAWINGS

Example embodiments of the present invention are described below, by way of example only, with reference to the accompanying drawings, in which FIG. 1 illustrates an example of an eye 150 and its six degrees of freedom of movement in relation to an ophthalmic apparatus;

Figure 10A:
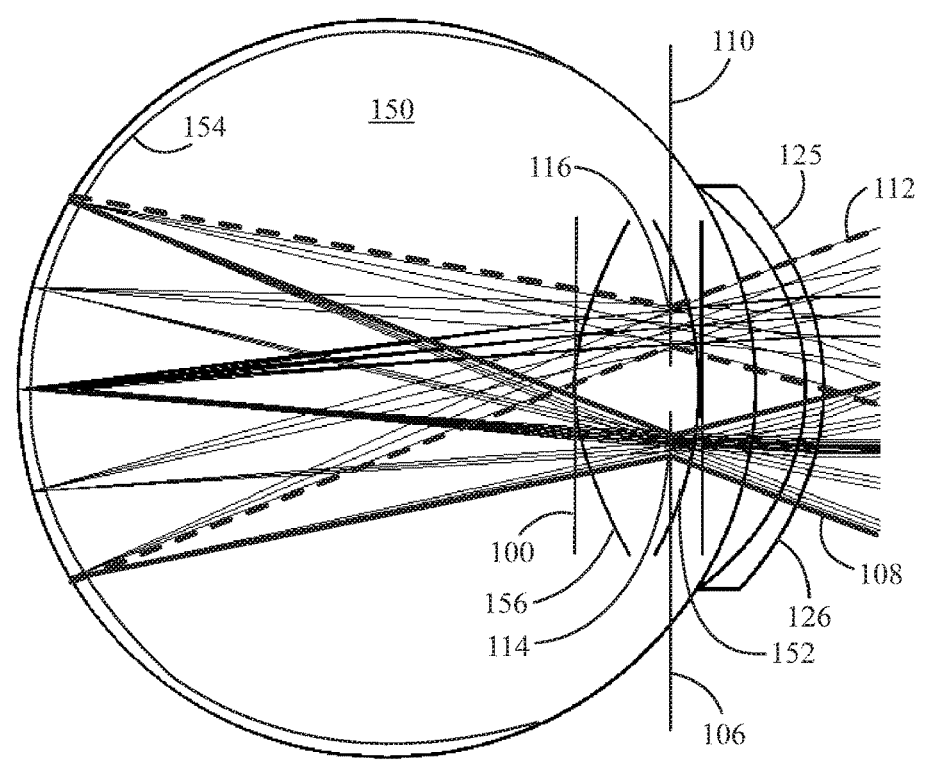
Figure 10B:
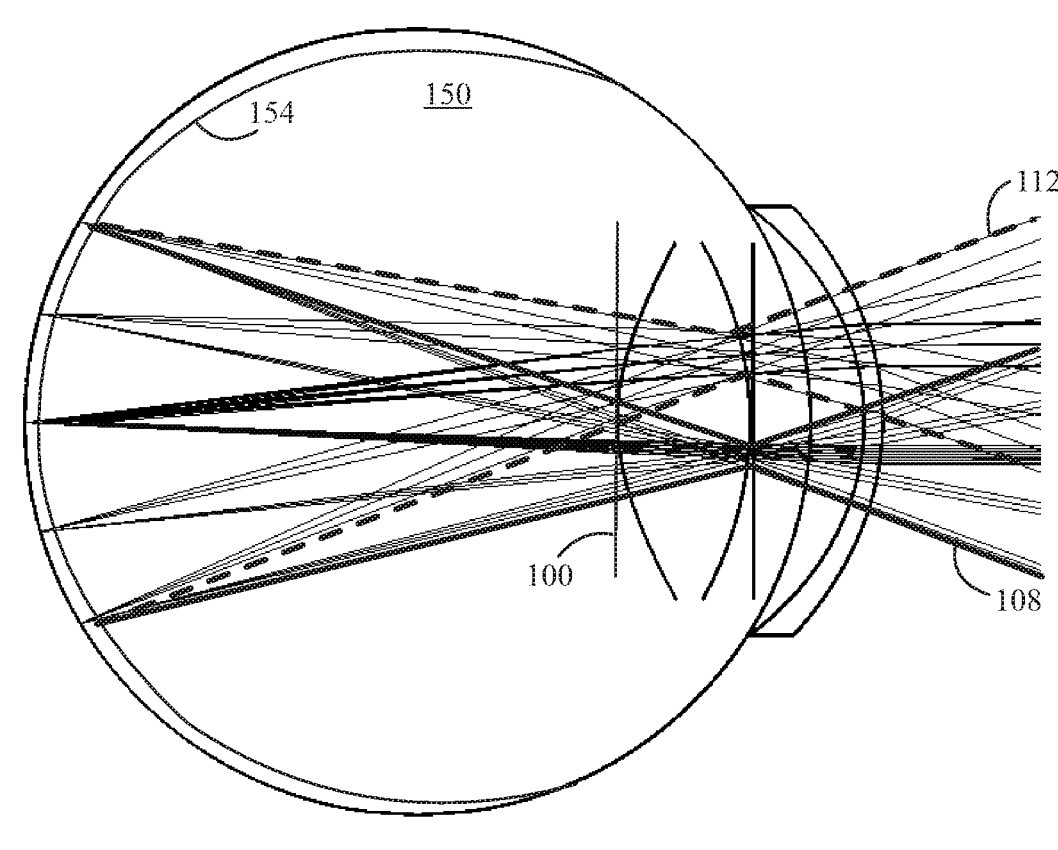
Figure 11A:
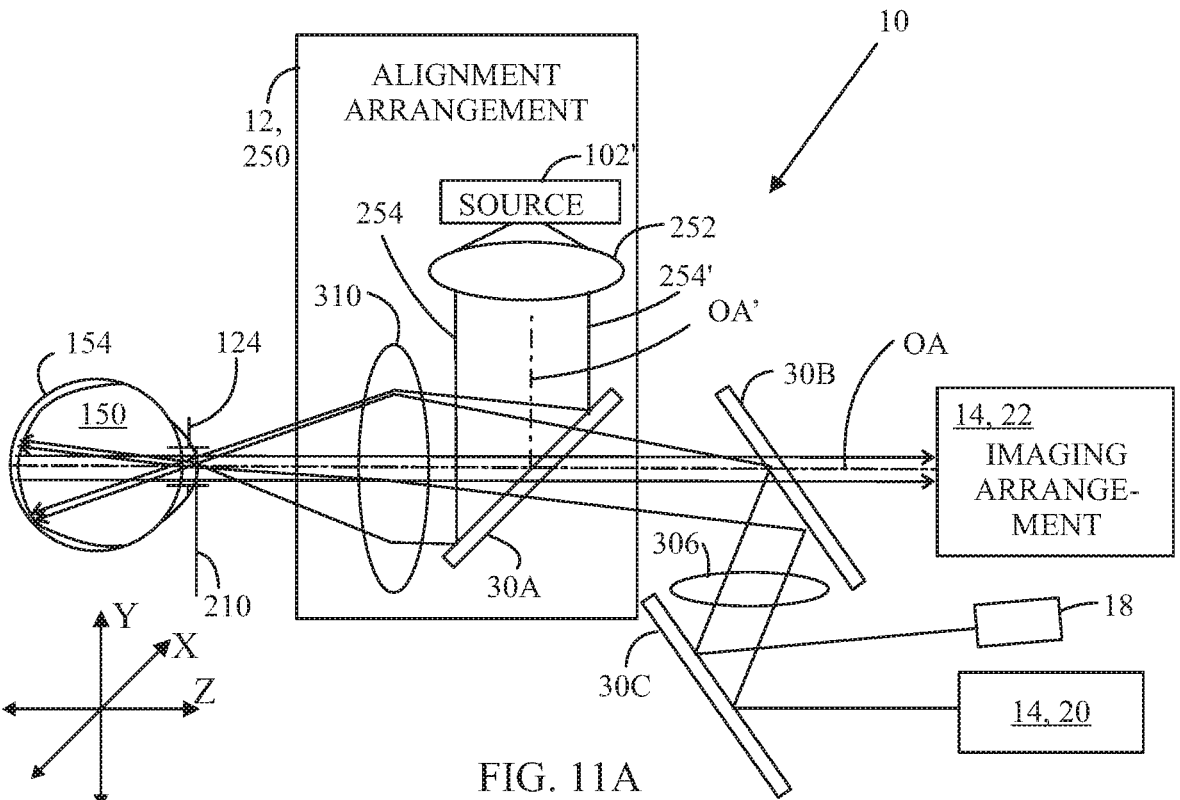
Figure 11B:
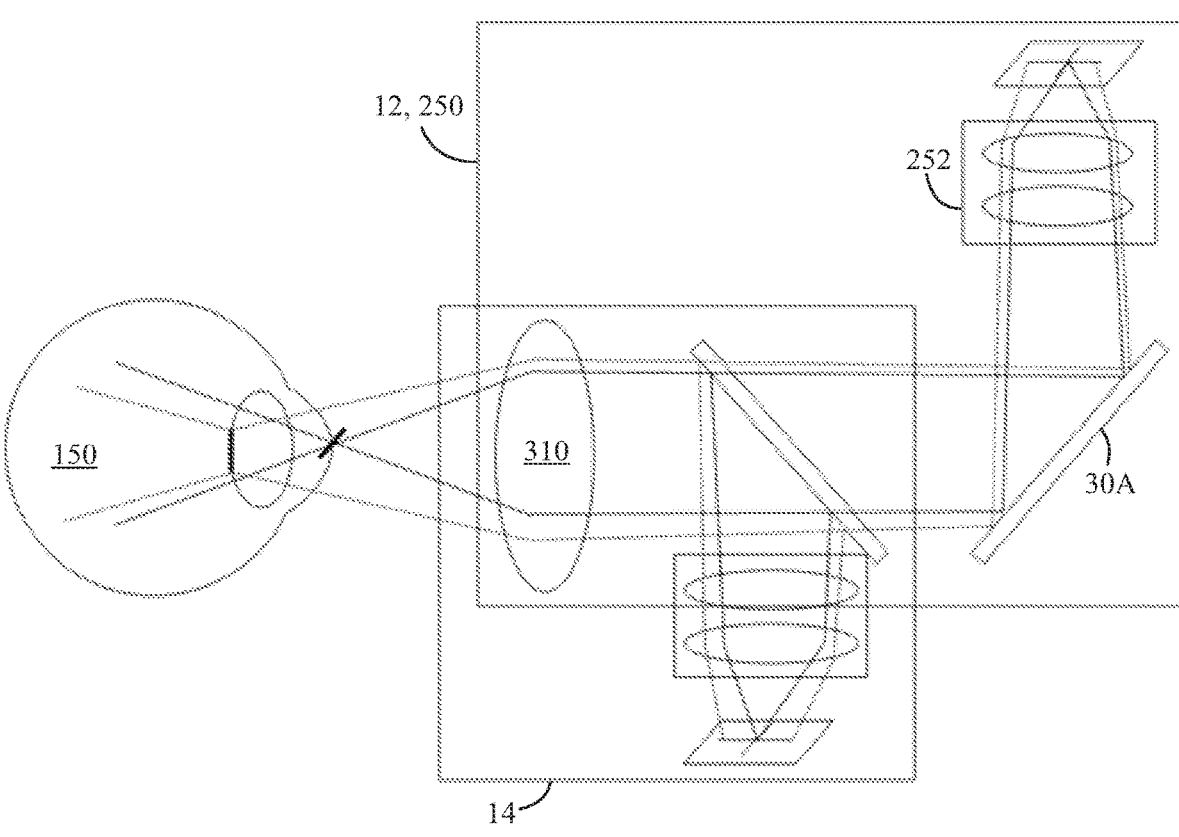
Figure 12:
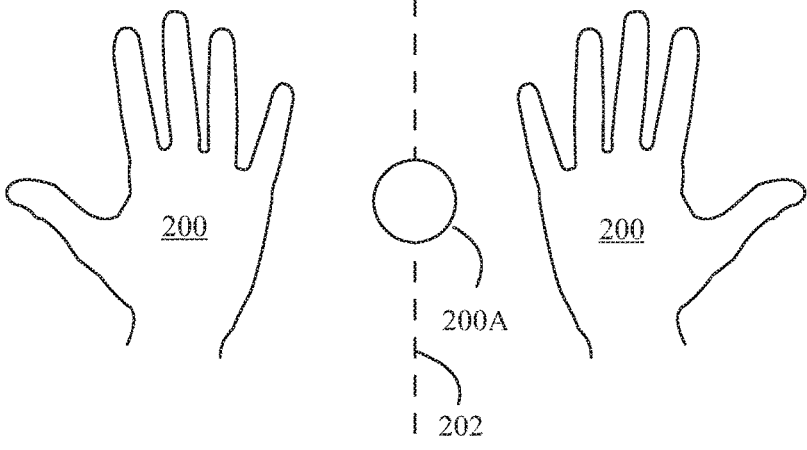
Figures 13, 14, 15:
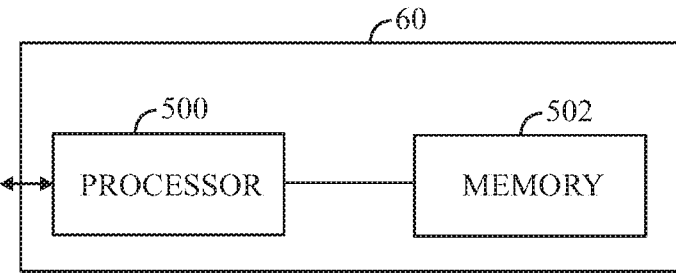

FIG. 10A to illustrates an example of eye alignment where Gullstrand principle is fulfilled;

FIG. 10B illustrates an example where Gullstrand principle is not fulfilled;

FIG. 11A illustrates an example of a cornea alignment;

FIG. 11B illustrates an example where a first alignment apparatus focuses a first line to the posterior surface of the eye, and the cornea alignment apparatus focuses a second line to the cornea;

FIG. 12 illustrates an example of a cornea alignment pattern;

FIG. 13 illustrates an example of cornea alignment light beam;

FIG. 14 illustrates an example of a block diagram of the ophthalmic apparatus with both the crystalline lens alignment and the cornea alignment;

FIG. 15 illustrates an example of the data processing unit; and

Figure 16:
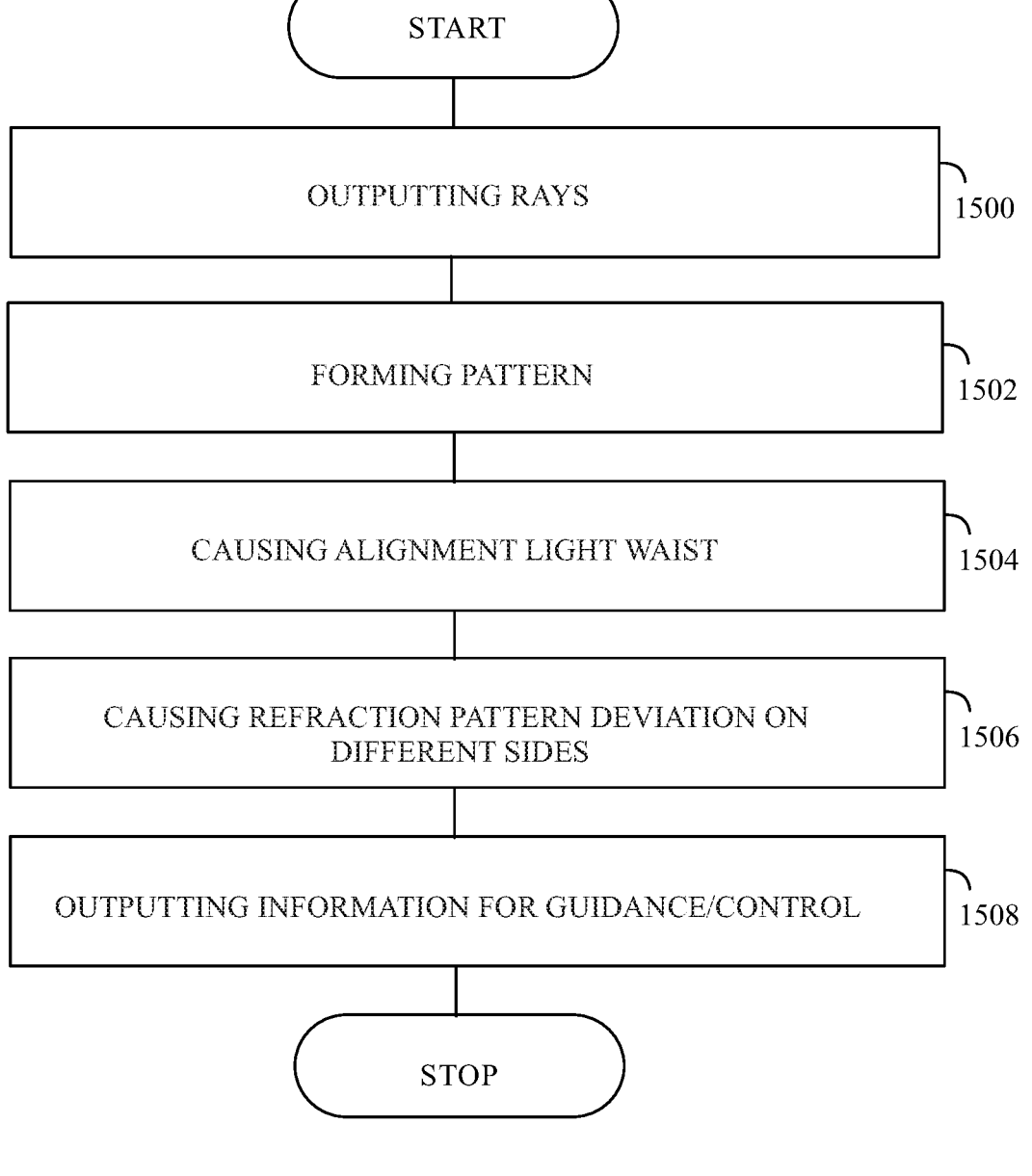

FIG. 16 illustrates of an example of a flow chart of an alignment method.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment.

The articles "a" and "an" give a general sense of entities, structures, components, compositions, operations, functions, connections or the like in this document. Note also that singular terms may include pluralities.

Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

The term "about" means that quantities or any numeric values are not exact and typically need not be exact. The reason may be tolerance, resolution, measurement error, rounding off or the like, or a fact that the feature of the solution in this document only requires that the quantity or numeric value is approximately that large. A certain tolerance is always included in real life quantities and numeric values.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1:
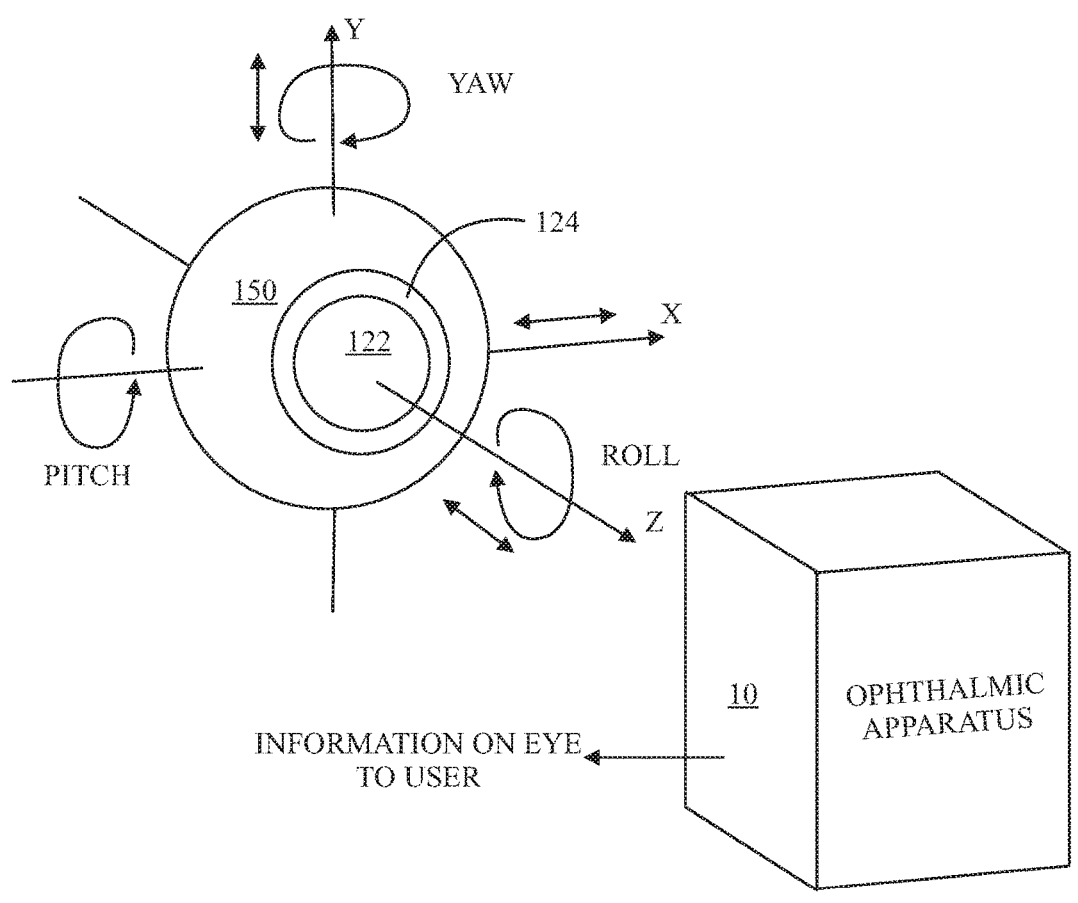

FIG. 1 illustrates an example of an eye 150 and its six degrees of freedom of movement in relation to the ophthalmic apparatus 10. Namely, the eye 150 may move back and forth along the spatial X-, Y- and Z-axis. Additionally, the eye 150 may rotate around the X-, Y- and Z-axis which can be defined in angular coordinates as pitch, yaw and roll. In this example, the X-axis denotes a horizontal axis, Y-axis denotes a vertical axis, the X-axis and the Y-axis being orthogonal to the Z-axis. The Z-axis denotes the axis spanning parallel to a direction between the eye 150 and the ophthalmic apparatus 10. The X-, Y- and Z-axes are orthogonal with respect to each other in this example.

In FIG. 1, the eye 150 of a person is in front of the ophthalmic apparatus 10. The eye 150 needs to be aligned in certain desired way relative to the ophthalmic apparatus 10 in order to utilize the ophthalmic apparatus 10 properly. A proper use of the ophthalmic apparatus 10 may mean that visual and/or optical observation and/or examination may be made by a user.

An eye alignment means that the eye 150 has been oriented and positioned to match certain values or ranges of these X-, Y- and Z-coordinates. The targeted alignment accuracy for each dimension may depend on the ophthalmic apparatus 10, desired case for which the ophthalmic apparatus 10 is used and the eye. For example for imaging of the fundus of the eye, the alignment accuracy may vary from approximately +/−1 mm to approximately +/−0.2 mm in X-, Y- and Z-coordinates.

Figure 2:
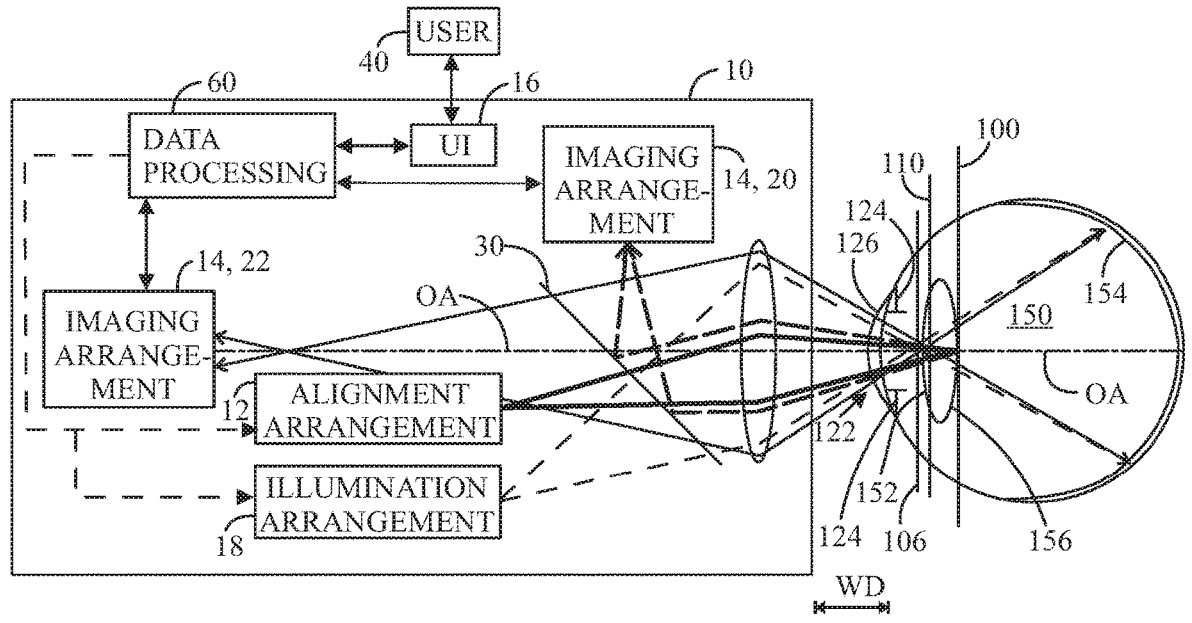
FIG. 2 illustrates an example of an ophthalmic apparatus.

With a reference to FIG. 2, a standard model of the eye 150 includes a retina 154 and an iris 124, which forms approximately a circular iris aperture i.e. a pupil 122, whose diameter may typically vary from a few millimeters up to 10 mm, typically between 3 and 8 mm, a crystalline lens 152 and the cornea 126.

The standard theoretical eye model may be based on an Emsley model, Emsley-Gullstrand model, or Liou and Brennan schematic eye model, for example. The eye model may be similar to an anatomical and optical eye. It may have a power of about 60.4 D and an axial length of about 24 mm for example. The eye model may be used to estimate alignment and other optical properties of the eye in a visible and near-infrared range of light, or for example between about 300 nm-about 1000 nm wavelength range. In an embodiment, the eye model may have variation depending on a size of a person that is examined, sex and age especially when it is a question of a child, for example. That is, the eye model may be selected based on anatomical and/or optical information on the person(s) to be examined.

Sufficient horizontal and vertical alignments (yaw and pitch) may be arranged such that the ophthalmic apparatus 10 generates a fixation target in the person's field-of-view, and the person is instructed to aim his/her eyes to the fixation target. The fixation target may be arranged such that it guides the eye 150 to a proper yaw and pitch angularly.

Proper rotational alignment (roll) may be achieved by the help of the set-up how the person is positioned in respect to the ophthalmic apparatus 10 as a whole. For example, if the person is standing or sitting, the roll-angle of the eye 150 may be known with sufficient accuracy and ophthalmic apparatus 10 can be aligned accordingly. For further adjusting the roll-angle, the ophthalmic apparatus 10 may also generate a target figure in the person's field-of-view, and the person is instructed to rotate his/her head such that the target figure is in a certain rotation. In many ophthalmic apparatuses 10, such as fundus cameras, the accurate alignment of roll is not needed but a rough roll alignment is enough.

With instruments which image the fundus 154 of the eye 150, sufficient orientational alignment (yaw, pitch, roll) may be achieved by recognizing features from the image of the fundus 154, such as fovea, macula or optic disc, and using that information for aligning the instrument orientation in respect to the eye 150.

Sufficient alignment in respect to the X- and Y-axes may be achieved for example by using a camera which captures an image of the iris during the alignment process, and by using an image recognition algorithm for measuring the position of the iris from the captured image for guiding the alignment towards the desired X- and Y-positions.

Sufficient alignment in respect to the X- and Y-axes, per se, may also be based on the prior art.

With fundus cameras still another method for alignment in X- and Y-axes may be used to recognize vignetting and/or other artifacts from the fundus images captured during the alignment process, and use that information to deduce corrective alignment moves, for example by using image processing and/or artificial intelligence algorithms, or user-learned experience.

The following concentrates on the alignment with respect to the Z-axis and a distance between the ophthalmic apparatus 10 and the eye 150 that is observed and/or examined, the distance being measured along the Z-axis.

FIG. 2 illustrates the ophthalmic apparatus 10. An alignment arrangement 12 of the ophthalmic apparatus 10, which refers to alignment in general, outputs rays of alignment light of a first alignment pattern 50. The alignment light is optical radiation, which may be visible and/or infrared light. In an embodiment, the alignment light is infrared in order to not cause constriction of the pupil of the eye 150. The ophthalmic apparatus 10 outputs rays of the alignment light in a converging manner toward a first target plane 100. The first target plane 100 may be flat or curved as understandable to a person skilled in the art of the optics. An optical arrangement of the ophthalmic apparatus 10 defines an optical distance of the first target plane 100 from the ophthalmic apparatus 10. The optical distance of the first target plane 100 from the ophthalmic apparatus 10 is made suitable for a working distance WD of the ophthalmic apparatus 10, and a person skilled in the art is familiar with the working distances WD of ophthalmic apparatuses, per se.

The first alignment pattern 50 is an illuminated figure and/or a constellation of one or more spots. The spots may be illuminated or the spot may be non-illuminated while their surrounding is illuminated. The illuminated figure may be a geometrical shape, for example. The figure and/or spots may be seen, observed or detected on a surface when the alignment light reflects from the surface. Examples of first alignment patterns 50 are illustrated in FIGS. 3 to 5.

Figure 3:
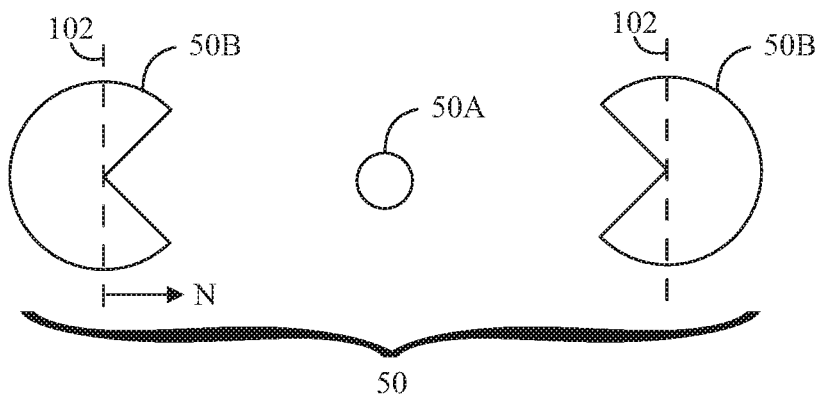
FIGS. 3 to 5 illustrate examples of alignment patterns.
Figure 4:
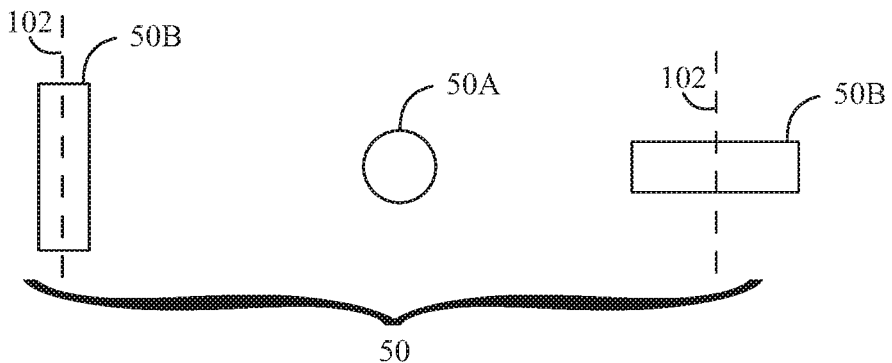
Figure 5:
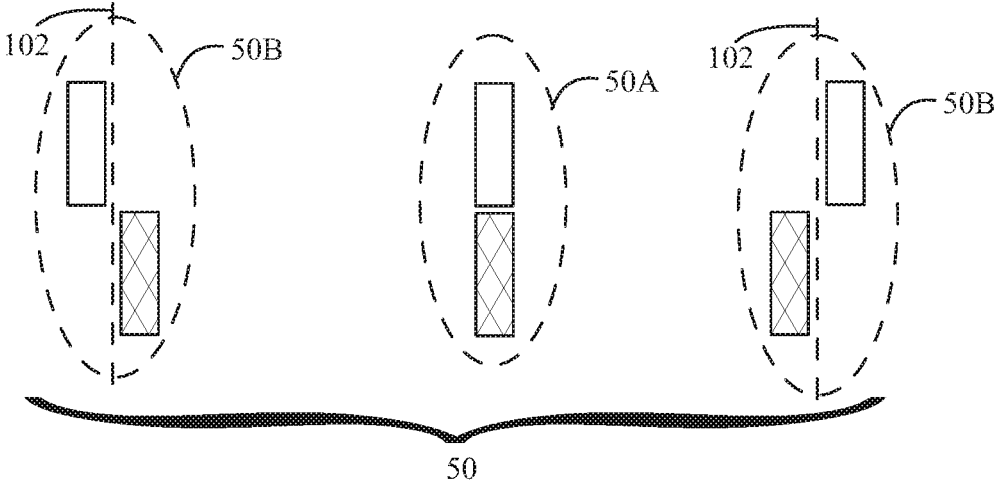

The alignment arrangement 12 forms a predetermined reflection pattern 50A of the first alignment pattern 50 on said first target plane 100 based on the convergence as shown in examples of FIGS. 3 to 5.

Figure 9:
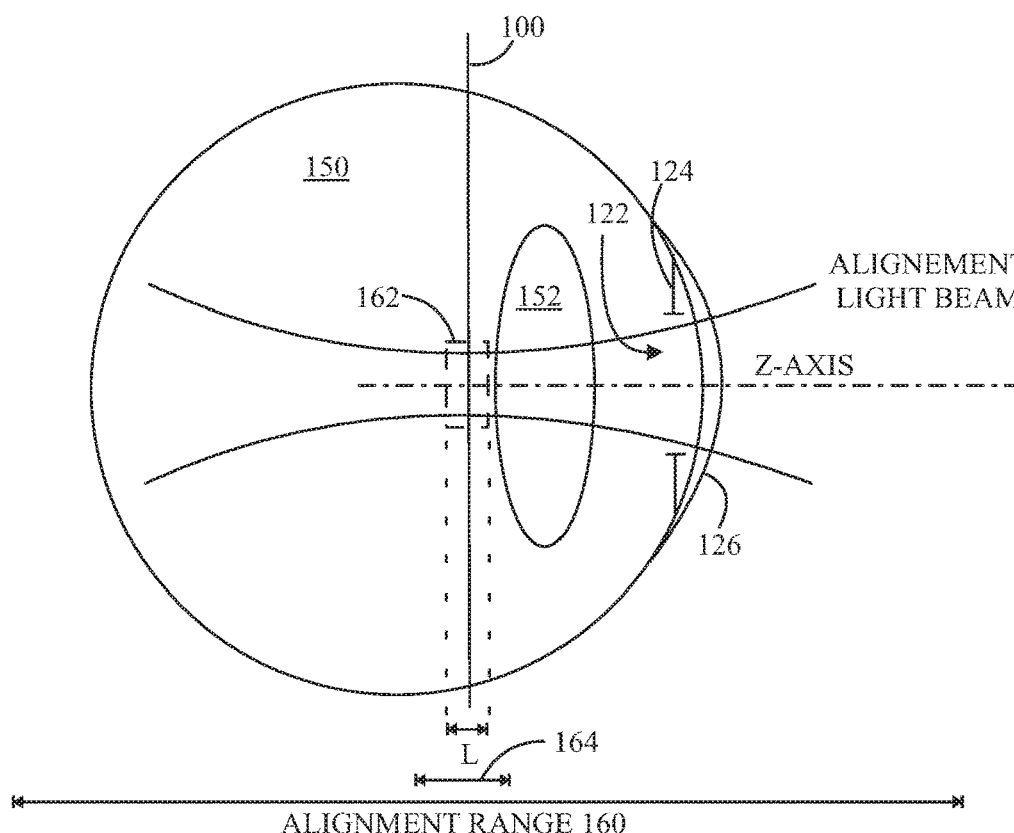
FIG. 9 illustrate an example of waist of the alignment light with respect to a first target plane that depends on optics of the ophthalmic apparatus.

As shown in example of FIG. 9, the alignment arrangement 12 causes the rays of the alignment light to have an alignment light waist zone 162 that includes the first target plane 100. That is, a distance between a point of the waist zone 162 and the ophthalmic apparatus 10 is the same as a distance between the first target plane 100 and the ophthalmic apparatus 10. At the alignment light waist zone 162, an area of a cross section of the alignment light beam reaches its minimum. The length of the minimum cross section of the alignment light that is the waist zone 162 extending in the direction of the Z-axis may include only one point or it may have a limited length L depending on how the rays of light are arranged to converge toward the first target plane 100. The first target plane 100 is within the waist zone 162. In an embodiment, a cross-sectional diameter of the alignment light waist zone 162 may be between one tenth of millimeter and about 2 mm or a few tenths of millimeters and about 2 mm, for example. in an embodiment, a cross-sectional diameter of the alignment light waist zone 162 may be about 1 mm, for example. Note that the rays of the alignment light do not necessarily intersect each other at the first target plane 100 although they may.

As illustrated in examples of FIGS. 3 to 5, the alignment arrangement 12 causes a reflection pattern 50B of the first alignment pattern 50 outside the first target plane 100 to deviate from the predetermined reflection pattern 50A based on the convergence. The reflection pattern 50B has a definite or distinctive form different from that of the predetermined reflection pattern 50A, and the predetermined reflection pattern 50A differs from the reflection pattern 50B in size and/or shape. Note that the predetermined reflection pattern 50A and the reflection pattern 50B are both reflections from a surface. However, the predetermined reflection pattern 50A is the target, which is searched for.

Note that although the patterns 50A and 50B are depicted as sharp edged, they may be blurred such as obscure and/or out of focus, in practice. Due to the convergence, the patterns 50B may be more blurred than pattern 50A, for example.

As illustrated in the example of FIG. 2, an imaging arrangement 14, which in FIG. 2 refers to imaging in general, is optically in the working distance WD from the eye 150 for a capture of an image or observation of an interior part of the eye 150 in response to a formation of the predetermined reflection pattern 50A of the first alignment pattern 50 on a posterior surface 156 of the crystalline lens 152 of the eye 150. When the predetermined reflection pattern 50A of the first alignment pattern 50 is formed on a posterior surface 156 of the crystalline lens 152 of the eye 150, it indicates that the posterior surface 156 of the crystalline lens 152 of the eye 150 is optically located at the first target plane 100. When the imaging arrangement 14 is optically in the working distance WD from the eye 150, an image of the interior of the eye 150 may be taken or an image of the interior of the eye 150 may be observed. The ophthalmic apparatus 10 may be close to the optimal working distance WD minimizing image artifacts, such as unwanted reflections for example, from the image or from the observation, when the posterior surface 156 of the crystalline lens 152 of the eye 150 is optically located at the first target plane 100. The image or the observation may have of desired resolution. The image the interior of the eye 150 may be in focus when the posterior surface 156 of the crystalline lens 152 of the eye 150 is optically located at the first target plane 100.

The interior part of the eye is at least at one location in a range from a crystalline lens 152 to fundus 154 of the eye 150, the range including the fundus 154 but not any part or surface of the crystalline lens 152. In an embodiment, the interior part of the eye 150 refers to the fundus 154.

A communication interface 16 of the ophthalmic apparatus 10, where the communication interface 16 may be a user interface 16 of the ophthalmic apparatus 10, outputs information on the reflection pattern 50B of the first alignment pattern 50 reflected from said posterior surface 156 when the ophthalmic apparatus 10 is directed toward the eye 150. In this manner, a user 40 is guided based on the reflection pattern 50B and the predetermined reflection pattern 50A of the first alignment pattern 50. The reflection pattern 50B is varying on said posterior surface 156. More in detail, the first alignment pattern 50 is varying with the position of the posterior surface 156 of the crystalline lens 152 and it helps the user 40 finding the working distance WD between the eye 150 and the ophthalmic apparatus 10 such that the predetermined shape 50A of the first alignment pattern 50 can be made to be on said posterior surface 156 of the crystalline lens 152.

The communication interface 16, which may comprise a screen, a keyboard, a mouse and/or a touchscreen or any other type of indicators including audio for outputting data. The communication interface 16 may also be used to input data to the ophthalmic apparatus 10. The communication interface 16 can also include one or more separate keys and buttons to launch actions such as still image capture or focusing. The screen and/or the touchscreen may belong to the monitor, for example.

In an embodiment, the user 40 is a human being. In an embodiment, the user or operator may be an automatic device. The communication interface 16 may communicate with the user 40, the user being an automatic device and/or a human being. Here the user 40 may refer to one or more people and/or one or more automatic devices. The ophthalmic apparatus 10 may communicate with an automatic or autonomous device where a human user is replaced by automation or the human user may be working independently and/or in cooperation with the automatic or autonomous user device. The user, human or automat, may also not be physically present next to the ophthalmic apparatus 10, but may be in different location and operate the ophthalmic apparatus 10 remotely.

The imaging arrangement 14 may also comprise an alignment imaging apparatus 20, which may capture and/or form an image of the reflection of the alignment light from a surface of the eye, such as the posterior surface 156 of the crystalline lens 152, or the cornea 126. The ophthalmic apparatus 10 may comprise abeam splitter 30 which reflects the light coming from the eye 150 to the alignment imaging apparatus 20.

The alignment imaging apparatus 20 may capture and/or form focused image from the first target plane 100. By that way, when there is a surface, such as an optical interface, at the first target plane 100 which reflects at least portion of the alignment light towards the alignment imaging apparatus 20, the captured and/or formed image represents a cross-section of the first alignment pattern 50 at the first target plane 100. When the reflecting surface, such as an optical interface, is off-set from the first target plane 100 by distance dz in Z-dimension, from the specularly reflected portion of the reflected light, the captured and/or formed image reproduces the cross-section of the first alignment pattern 50 at double distance 2*dz from the first target plane 100, on the same side of the first target plane 100 as the reflecting surface. For diffuse reflected portion of the reflected light, the captured and/or formed image reproduces the cross-section of the first alignment pattern 50 on the reflecting surface. When the reflecting surface has curvature, the distance from the imaged cross-section to the first target plane 100 differs from 2*dz but still the distance can be calculated from the curvature as known by a person skilled in art of optics. Thus, the captured and/or formed image generally represents the cross-section of the first alignment pattern 50 only when the reflecting surface coincides with the first target plane 100. When the form of the first alignment pattern 50 is known before, at, and after the first target plane 100, the captured and/or formed image can be used to deduce the position of the reflecting surface related to the first target plane 100. The alignment imaging apparatus 20 may comprise an image sensor such as CMOS or CCD sensor (complementary metal-oxide-semiconductor or charge-coupled device), for example. Instead of capturing and/or forming image, the alignment imaging apparatus 20 may use any other detection means for detecting properties of the light reflected from the eye. The alignment imaging apparatus 20 may comprise at least one light detector element, such as silicon photodiode for example, or an array of light detector elements.

A reflection pattern 50B is formed from such light of the first alignment pattern 50, which is reflected from an optical interface towards the ophthalmic apparatus 10.

The alignment imaging apparatus 20 is arranged to detect how much the reflection pattern 50B resembles the prede-termined reflection pattern 50A, and possibly how the reflection pattern 50B differs from it, in order to deduce a relation between a position of the reflecting surface and the first target plane 100.

Each of FIGS. 3 to 5 illustrates examples of the first alignment pattern 50 on one side of the first target plane 100, at the target plane 100 and on an opposite side of the target plane 100 from left to right.

Figure 6A:
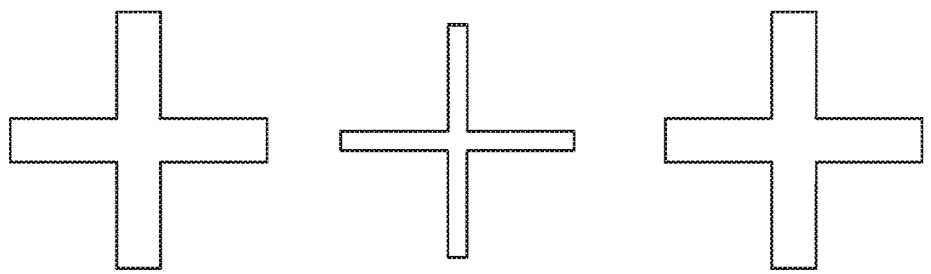
FIGS. 6A and 6B illustrate example of illumination patterns and constellation of spots.
Figure 6B:
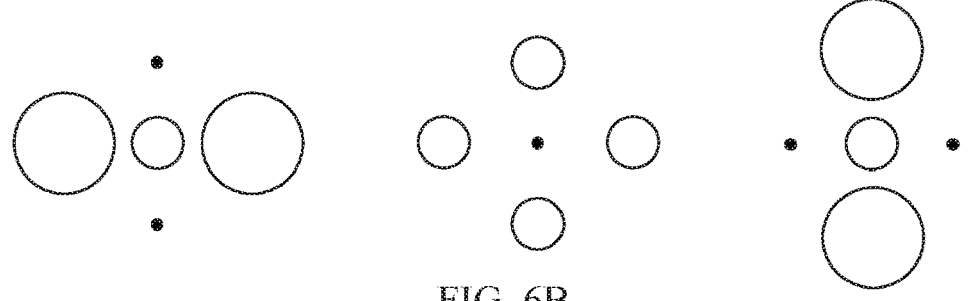

FIGS. 6A and 6B illustrate examples of illumination patterns and constellation of spots. The cross at the left side in FIG. 6A illustrate the illumination pattern when the ophthalmic apparatus 10 is too far from the eye 150. The cross at the middle in FIG. 6A illustrate the illumination pattern when the ophthalmic apparatus 10 is at the working distance from the eye 150. The cross at the right side in FIG. 6A illustrate the illumination pattern when the ophthalmic apparatus 10 is too close to the eye 150. In a corresponding manner, the circular spots at the left side in FIG. 6B illustrate the illumination pattern when the ophthalmic apparatus 10 is too far from the eye 150. The circular spots at the middle in FIG. 6B illustrate the illumination pattern when the oph-thalmic apparatus 10 is at the working distance from the eye 150. The circular spots at the right side in FIG. 6B illustrate the illumination pattern when the ophthalmic apparatus 10 is too close to the eye 150. In the example of FIG. 6A, it is not possible to know from the crosses if the ophthalmic appa-ratus 10 is too far or too close to the eye 150 because the crosses at the left and at the right look similar. However, it is possible to distinguish if the ophthalmic apparatus 10 is too close to or too far from the eye 150 based on the circular spots because the circular spots look different depending on the distance between the ophthalmic apparatus 10 and the eye 150.

In the other words, the alignment arrangement 12 of the ophthalmic apparatus 10 outputs rays of alignment light of a first alignment pattern 50. The middle figures of FIGS. 6A and 6B represent the cross-section of the alignment light at the first target plane 100, i.e. represent the illumination pattern on the posterior surface 156 of the crystalline lens 162 when eye 150 is at the desired working distance. The left-side figures of FIGS. 6A and 6B represent the cross-section of the alignment light on the other side of the first target plane 100 than the ophthalmic apparatus 10, i.e. they represent the illumination pattern on the posterior surface 156 of the crystalline lens 162 when the ophthalmic appa-ratus 10 is too far from the eye 150. The right-side figures of FIGS. 6A and 6B represent the cross-section of the alignment light on the same side of the first target plane 100 as the ophthalmic apparatus 10, i.e. they represent the illumination pattern on the posterior surface 156 of the crystalline lens 162 when the ophthalmic apparatus 10 is too close to the eye 150.

Still, the middle figures of FIGS. 6A and 6B may resemble the image captured by of an image capturing device such as a camera of the alignment image apparatus 20 when the eye 150 is at the desired working distance. The left-side figures of FIGS. 6A and 6B may resemble the image captured by an image capturing device such as a camera of the alignment image apparatus 20 when the ophthalmic apparatus 10 is too far from the eye 150. The right-side figures of FIGS. 6A and 6B may resemble the image captured by an image capturing device such as a camera of the alignment image apparatus 20 when the ophthalmic apparatus 10 is too close to the eye 150.

Figure 7A:
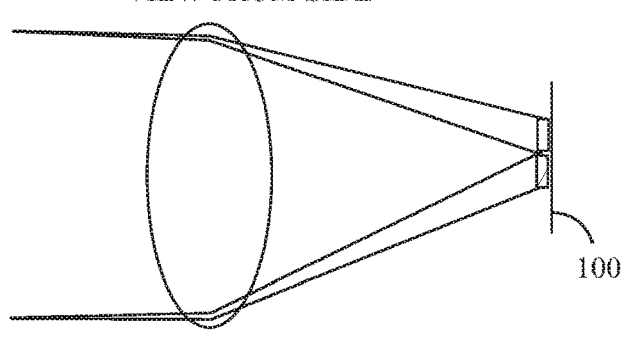
FIGS. 7A and 7B illustrate examples of convergence of alignment light in transverse directions.
Figure 7B:
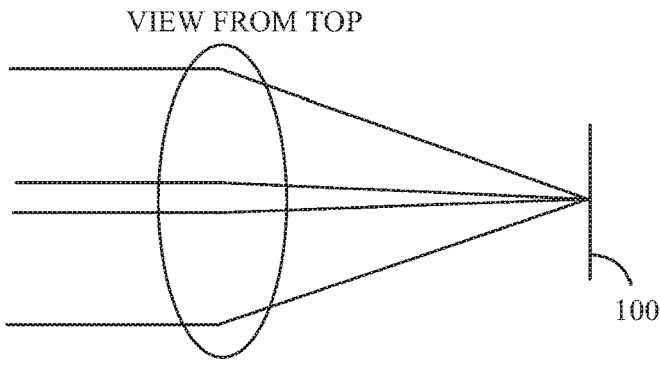

FIGS. 7A and 7B illustrate examples how light is made to converge in transverse or orthogonal dimensions. When looking from side as in FIG. 7A, portions of the alignment pattern 50 are one above other like also shown in FIG. 5. However, when looking from top or bottom as in FIG. 7B, the portions of the alignment pattern 50 are formed one on another. The upper and lower portions of the alignment pattern 50 propagate on average to different directions in a horizontal dimension, which may cause the first alignment pattern 50 to behave as depicted in FIG. 5, i.e. positions of upper and lower lines of the first alignment pattern 50 in relation to each other are opposite on opposite sides of the target plane 100, and the lines are aligned with each other at the first target plane 100.

Figure 8A:
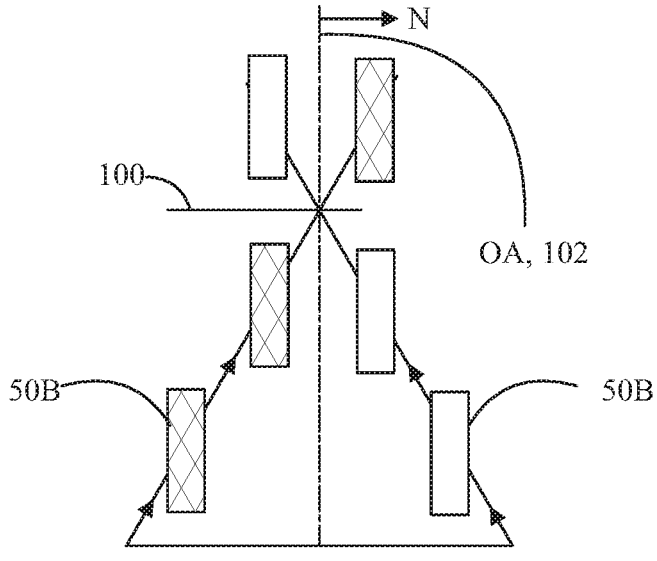
FIGS. 8A and 8B illustrate additional examples of convergence of alignment light.
Figure 8B:
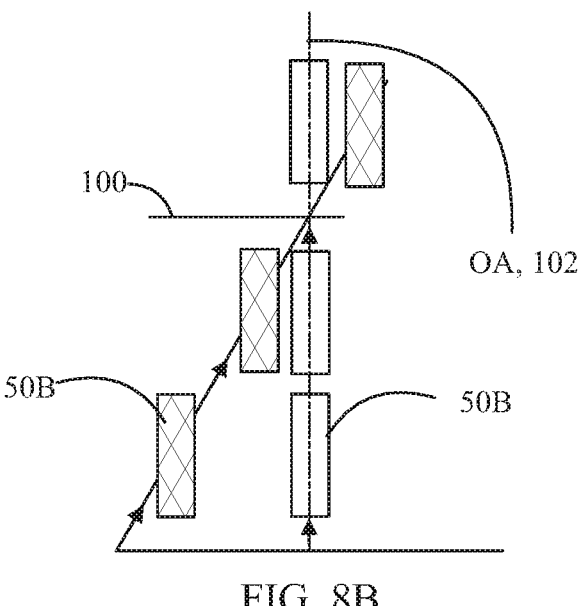

FIGS. 8A and 8B also illustrate examples of how light is made to converge. In FIG. 8A, light of the reflection pattern 50B (it is seen as a reflection on a surface) is transmitted in the converging manner toward the first target plane 100, and a portion of the reflection pattern 50B is first on left side but swaps to the right side at the first target plane 100. Corre-spondingly, light of the reflection pattern 50B is transmitted in the converging manner toward the first target plane 100, and a portion of the reflection pattern 50B is first on right side but swaps to the left side at the first target plane 100.

In FIG. 8A, light of the reflection pattern 50B is trans-mitted in the converging manner toward the first target plane 100, and a portion of the reflection pattern 50B is first on left side but swaps to the right side at the first target plane 100. Light of another portion of the reflection pattern 50B is transmitted directly forward toward the first target plane 100, and it does not swap sides. However, the portions of the reflection pattern 50B swap sides at the first target plane 100. The swapping causes the reflection pattern 50B altogether be different in different sides of the first target plane 100.

In an embodiment examples of which are illustrated in FIGS. 3 and 8B, the first alignment pattern 50 may have a difference in shape, structure and/or color on opposite sides of a division plane 102 a normal N of which is perpendicular to an optical axis OA of the alignment arrangement 12 in order to cause the reflection pattern 50B of the first align-ment pattern 50 on one side of the first target plane 100 to deviate from the reflection pattern 50B of the first alignment pattern 50 on the other side of the target plane 100. In that manner the reflection pattern 50B also deviates from the predetermined reflection pattern 50A. Alternatively or addi-tionally as illustrated in FIG. 4, the alignment arrangement 12 may cause a different convergence of the alignment light on opposite sides of the division plane 102 in order to cause the reflection pattern 50B of the first alignment pattern 50 outside the first target plane 100 to deviate from the prede-termined reflection pattern 50A, which is formed on the first target plane 100.

In an embodiment example of which are illustrated in FIGS. 3 to 8B, the alignment arrangement 12 may cause the shape of the reflection pattern 50B on one side of the first target plane 100 to be different from the shape of the reflection pattern 50B on the opposite side of the first target plane 100 based on the convergence. The difference may be reflection symmetrical like in FIGS. 3, 5 and 8A and 8B or rotation symmetrical like in FIG. 4, for example.

The reflection symmetrical difference may be caused by a convergence output of a reflection asymmetric figure. The line of reflection is then the same as the division plane.

The rotational symmetry may be achieved by at least one biconic optical element, such as a cylindrical lens or cylindrical mirror, for example. When one or more non-cylindrical and real image forming lenses are used with the at least one biconic optical element, a result as shown in FIG. 4 can be achieved. Also two cylindrical lenses crossed with respect to each other can be used to achieve a result similar to that in FIG. 4.

By using at least one biconic optical element the first alignment pattern 50 can be arranged to project a spot on the first target plane 100 with purposefully introduced astigmatism. That astigmatism spreads the spot more to one direction (for example, to vertical direction) before the first target plane 100 and more to the another direction (for example, to horizontal direction) after the first target plane 100.

Instead of astigmatism, spherical aberration, longitudinal chromatic aberration, or any asymmetry in illumining beam axial direction, or in the angular distribution, for example, may be used to introduce structure to the first alignment pattern 50 such that it varies in a predetermined manner as a function of the Z-axis before, at, and after the first target plane 100.

The communication interface 16 of the ophthalmic apparatus 10 may output information on the shape of the reflection pattern 50A, 50B reflected from said posterior surface 156 when the ophthalmic apparatus 10 is directed toward the eye 150 for guiding the user 40. Based on the guidance, the user 40 may select a direction of the alignment in order to align, in a direction parallel to the Z-axis, the eye 150 and the ophthalmic apparatus 10 with respect to each other based on the shape of the reflection pattern 50B that is varying as a function of distance between the eye 150 and the ophthalmic apparatus 10 on the posterior surface 156 of the crystalline lens 162. That means that the first alignment pattern 50 is varying with the position of the posterior surface 156 of the crystalline lens 152. The guidance helps the user 40 finding the working distance WD or controls the user 40 to advance toward the working distance WD. The direction of alignment adjustment depends on the shape of the reflection pattern 50B as illustrated in FIGS. 3 to 5. The shape on the left refers to a too short distance between the eye 150 and the ophthalmic apparatus 10. The shape in the middle refers to a correct or desired distance between the eye 150 and the ophthalmic apparatus 10. The shape on the right refers to a too long distance between the eye 150 and the ophthalmic apparatus 10. Hence, the variation of the shape not only indicates if the distance between the eye 150 and the ophthalmic apparatus 10 is correct or not but it also indicates a direction toward which a corrective move should or could be made.

The ophthalmic apparatus 10, an example of which is illustrated in FIG. 11, may comprise an illumination arrangement 18 that directs illumination light through an illumination path 108 toward a second target plane 106 where the illumination light has an illumination path waist 114. The illumination path waist 114 may be similar to the waist 162 of the alignment light which is illustrated in FIG. 9. A waist zone related to the illumination path waist 114 may be a point or it may extend over a length. The second target plane 106 may differ from the first target plane 100. However in one or more embodiments, the first and second target planes 100, 106 may be coplanar.

As illustrated in FIG. 2 and FIGS. 10A to 10B, the imaging arrangement 14 of the ophthalmic apparatus 10 may additionally comprise an examination imaging apparatus 22, which is configured to receive a reflection of the illumination light from the interior part of an eye 150 through the reception path 112. A part of the light reflected from the eye 150 passes through the beam splitter 30 and propagates to the examination imaging apparatus 22. In an embodiment, the examination imaging apparatus 22 and alignment imaging apparatus 20 may exchange their places. The reception path 112 has a reception path waist 116 at a third plane 110. The reception path waist 116 may be similar to the waist 162 of the alignment light which is illustrated in FIG. 9. A waist zone related to the reception path waist 116 may be a point or it may extend over a length. The illumination path 108 and the reception path 112 of the examination imaging apparatus 22 are separated from each other at and between the second and third planes 106, 110, which are between the first target plane 100 and the ophthalmic apparatus 10. The third target plane 110 may differ from the first target plane 100. However in one or more embodiments, the first and third target planes 100, 110 may be coplanar, or coplanar within about 1 mm distance, for example. The third target plane 110 may differ from the second target plane 106. However in one or more embodiments, the second and third target planes 106, 110 may be coplanar, or coplanar within about 1 mm distance, for example.

In an embodiment, the illumination arrangement 18 may form the illumination path 108 with a cross sectional area smaller than a pupil 158 of the eye 150 at and between second and third planes 106, 110. A normal of the cross sectional area is parallel to the optical axis of the alignment light or the Z-axis. A diameter of the cross sectional area may be from a fraction of a millimeter up to about 10 mm, typically between about 0.5 and about 5 mm.

The examination imaging apparatus 22 may form the reception path 112 with a cross sectional area smaller than the pupil 158 of the eye 150 at and between the second and third planes 106, 110. A normal of the cross-sectional area is parallel to the optical axis of the alignment light or the Z-axis. A diameter of the cross-sectional area may be from a portion of millimeter up to about 10 mm, typically between about 0.5 and about 5 mm, for example The imaging arrangement 14 may receive the reflection of the rays of the alignment light from a surface within an alignment range 160 that is illustrated in FIG. 9. The alignment range 160 includes the first, second and the third target planes 100, 106 and 110 and it has a length that may vary with the design of the ophthalmic apparatus 10. A length of the alignment range 160 may be about between about 1 mm and 30 mm, or between bout 4 mm and 15 mm, for example, although it may be designed with an undefined length.

In an embodiment, the alignment arrangement 12 may form the alignment light waist region 162 smaller than about 1 mm, i.e. the length L in FIG. 9 is smaller than about 1 mm. The length L may be order of 0.1 mm or few tenths of millimeter in an embodiment. The first target plane 100 may then be within the alignment light waist region 162. A depth of focus of the alignment imaging apparatus 20 may be approximately similar to, or smaller than the alignment light waist region 162. In an embodiment, the depth of focus 164 of the alignment imaging apparatus 20 is longer than the alignment light waist region 162, extending up to few millimeters.

In an embodiment, the alignment arrangement 12 and the examination imaging apparatus 22 may be optically matched with each other in order to cause the examination imaging apparatus 22 to be in the working distance from the eye 150 in response to the formation of the predetermined shape 50A of the first alignment pattern 50 on the posterior surface 156 of the crystalline lens 152. The working distance may mean that the examination imaging apparatus 22 is in focus for the capture of a focused image of the fundus 154 of the eye 150. The formation of the predetermined shape 50A of the first alignment pattern 50 on the posterior surface 156 of the crystalline lens 152 indicates that the posterior surface 156 of the crystalline lens 152 of the eye 150 is at the first target plane 100.

In an embodiment, the illumination arrangement 18 may configured to illuminate and the examination imaging apparatus 22 may be configured to image the interior of an eye 150 based on the Gullstrand principle when the examination imaging apparatus 22 is at the working distance from the eye 150.

According to the Gullstrand principle, reflection and scatter from the illumination path 108 into the reception path 110 can be avoided by separating the illumination path 108 and the reception path 100 completely in the length from the outer surface of the cornea 126 to the posterior surface 156 of the crystalline lens 152. That is not necessarily always fully fulfilled but when the principle is close enough or at least approximately fulfilled, observation and examination of the eye 150 can be performed. During the observation and/or examination the distance between the eye 150 and the ophthalmic apparatus 10 can be selected such that a difference between the Gullstrand principle and the actual paths 108, 112 of illumination and reception is minimized or optimized.

FIG. 10A illustrates an example of a case where the illumination path 108 and the reception path 110 of a fundus camera fulfil the Gullstrand principle, i.e. the paths are separated from the outer surface 125 of the cornea 126 to the posterior surface 156 of the crystalline lens 152. This happens, when the posterior surface 156 of the crystalline lens 152 is close to the first target plane 100. In this case, the fundus images captured by the fundus camera are free of reflections from optical interfaces between these two surfaces 126, 156.

In an embodiment an example of which is illustrated in FIGS. 10A, 10B and 12, the alignment arrangement 12 may direct rays of light of a cornea alignment pattern 200 in a converging manner toward a fourth target plane 210. The alignment pattern 200 has a difference in shape, structure and/or color on opposite sides of a second division plane 202 of the cornea alignment pattern 200. A normal N of the division plane 202 of the cornea alignment pattern 200 is perpendicular to an optical axis OA of the alignment arrangement 12. Alternatively or additionally, the alignment arrangement 12 may converge the alignment light of the cornea alignment pattern 200 differently on opposite sides of the division plane 202 of the cornea alignment pattern 200. The cornea alignment pattern 200 is similar to the first alignment pattern 50. However, a predetermined pattern 50A of the first alignment pattern 50 is intended be reflected from the posterior surface of the crystalline lens 152 while a predetermined cornea alignment pattern 200A is intended be reflected from an outer surface of the cornea 126. This is similar to the alignment with respect to the posterior surface 156 of the crystalline lens 152 except now the alignment is performed utilizing the cornea 126. The crystalline lens 152 alignment and the cornea alignment may be performed together for further improving the alignment in the direction of the Z-axis.

For the purpose, the alignment arrangement 12 may comprise a cornea alignment arrangement 250 which forms the predetermined cornea alignment pattern 200A on said fourth target plane 210 based on the convergence.

In an embodiment an example of which is illustrated in FIG. 13, the cornea alignment arrangement 250 causes the rays of the cornea alignment light to have a cornea alignment light waist zone 262 that includes the fourth target plane 210 based on the convergence.

The cornea alignment arrangement 250 causes a shape of the cornea alignment pattern 200 to deviate from the predetermined cornea alignment pattern 200A outside the fourth target plane 210. The cornea alignment arrangement 250 may cause the shape of the cornea alignment pattern 200 on one side of the fourth target plane 210 to be different from the shape of the cornea alignment pattern 200 on the opposite side of the fourth target plane 210 based on the convergence.

The imaging arrangement 14 is optically at the working distance WD from the eye 150 for observation and/or a capture of an image of an interior part of an eye 150 at least at one location in a range from a crystalline lens 152 to the fundus 154 of the eye 150 in response to a formation of the predetermined cornea alignment pattern 200A on the cornea 126 of the eye 150, which indicates that the cornea 126 of the eye 150 is at the fourth target plane 210.

As illustrated in FIG. 11A the cornea alignment arrangement 250 may also comprise at least one initial lens 252 in an embodiment. Any of the at least one initial lens 252 may be an image forming lens, for example. Alternatively or additionally to the at least one initial lens 252, the cornea alignment arrangement 250 may comprise at least one mirror (not shown in Figs). Any of the at least one mirror may be an image forming mirror, for example. In an embodiment, the at least one initial lens 252 may collimate the beams 254, 254' of cornea alignment light of the cornea alignment pattern 200 with respect to each other, for example. In such a case, a projection of any one of the beams 254, 254' on a plane, a normal of which is perpendicular to the optical axis OA of the cornea alignment light apparatus 250, is parallel to a projection of any other of the beams 254, 254' on said plane within an aberration tolerance. In this embodiment, the alignment arrangement 250 may direct the beams 254, 254' of light via a beam splitter 30A toward the fourth plane 210 in a converging manner.

After the beam splitter 30A in a direction of propagation from the cornea alignment apparatus 250 toward the eye 150, the beams 254, 254' of the cornea alignment light may be pass through at least one objective lens 310. The at least one objective lens 310 may be common to the cornea alignment arrangement 250, the first alignment arrangement 12, the imaging arrangement(s) 14, 20, 22. In an embodiment, the cornea alignment arrangement 250 and the imaging arrangement 14, 22 may have separate objective lenses, although their optical axes OA, OA' should have a determined and known relation to each other in order to enable the alignment between the eye 150 and the ophthalmic apparatus 10. The optical axis OA' of the cornea alignment arrangement 250 and the optical axis OA of the imaging arrangement 14, 22 may be at least approximately coaxial between the eye 150 and the ophthalmic apparatus 10. The optical axis OA' of the cornea alignment apparatus 250 and the optical axis OA of the imaging apparatus 14, 22 may be at least approximately coaxial between the eye 150 and the beam splitter 30A.

The at least one objective lens 310 may cause an envelope of the rays of the alignment light of the first alignment pattern 50 to converge to and diverge from the waist Wc.

The at least one objective lens 310 may cause an envelope 105 of the beams 254, 254' of the cornea alignment light to converge to and diverge from the waist We as shown in FIG. 13.

In this manner, the beams 254, 254' of cornea alignment light approach each other and the optical axis OA between the ophthalmic apparatus 10 and the fourth plane 210. However, the beams 254, 254' of cornea alignment light do not necessarily intersect each other. In an embodiment, at least two of the beams 254, 254' of cornea alignment light intersect each other and/or the optical axis OA. This convergence can be caused together with the at least one initial lens 252 and the objective lens 310 in this example. Alternatively in other embodiments including embodiments where the cornea alignment arrangement 250 and the imaging apparatus 14, 22 have separate objective lenses, the convergence may be caused alone by the at least initial lens 252 or by a light manipulation arrangement (not shown in Figs), which is not image forming but merely directs separate rays of light.

FIG. 10A illustrates an example of the eye alignment between the eye 150 and the ophthalmic apparatus 10 in a situation, when the optical distance between the outer surface of the cornea 126 to the posterior surface 156 of the crystalline lens 152 is longer than in the case where the optical length between the illumination path 108 and the reception path 110 fulfils the Gullstrand principle. The eye 150 may be aligned such that a distance from the posterior surface 156 of the crystalline lens 152 to the first target plane 100 and a distance from the outer surface of the cornea 126 to the fourth target plane 210 are both minimized at the same time. In this manner, reflections from both the outer surface of the cornea 126 and the posterior surface 156 of the crystalline lens 152 may be minimized simultaneously.

When the information of the reflected patterns from the first alignment pattern 50 and from the cornea alignment pattern 200 indicate that the optical distance between the outer surface of the cornea 126 to the posterior surface 156 of the crystalline lens 152 is longer than the optical length between the illumination path 108 and the reception path 110 where Gullstrand principle is fulfilled, the user may adjust the paths 108, 110 farther apart increasing the optical length between the paths 108, 110 where Gullstrand principle is fulfilled, and so enabling the eye alignment as shown in FIG. 10A.

The ophthalmic apparatus 10 in FIG. 11A additionally comprises a second beam splitter 30B and a third beam splitter 30C. The second and third beam splitters 30B and 30C reflect light from the illumination arrangement 18 toward the eye 150. In a corresponding manner, the second and third beam splitters 30B and 30C reflect light from the eye 150 to the alignment imaging apparatus 20. Between the second and third beam splitters 30B, 30C there may be one or more optical elements 306.

FIG. 10B illustrates an embodiment where the first alignment apparatus 12 may focus a first line to the posterior surface of the eye 150 when the eye 150 is close to the optimal working distance from the eye 150, and the cornea alignment apparatus 250 focuses a second line to the cornea when the eye 150 is close to the optimal working distance from the eye 150. The first and the second line may be approximately perpendicular to each other. The first and the second lines may be formed by using separate optics and/or light source. The first alignment apparatus 12 and the second alignment apparatus 250 may also be integrated together by using at least one biconic optical element for forming focus of two approximately perpendicular lines to different distance from the at least one objective lens 310. Such at least one biconic optical element may comprise a biconic lens or mirror, such as cylindrical lens or mirror, or anamorphic prism, for example. The imaging arrangement 14 may comprise at least one biconic element for forming the image of the first line reflected from the posterior surface of the crystalline lens to the same sensor as the image of the second line reflected from the cornea. This kind of arrangement enables obtaining alignment information from both the crystalline lens posterior surface and the cornea simultaneously by using only one sensor and minimized number of optical elements.

The envelope of the rays of the alignment light of the first alignment pattern 50 may extend to large NA, such as >0.1, or >0.2 for example. That enables reflected light capture by the alignment imaging apparatus 20 even when the area of the posterior surface 156 of the crystalline lens 152 from which the light is reflected, is at large angle in respect to its optimal alignment. As a result, this large NA allows use of the described alignment method with large variations in eye alignment, and eye shape.

Similarly, for the same reason in respect to the cornea reflected light, the envelope of the rays of the beams 254, 254' of cornea alignment light may extend to large NA, such as >0.1, or >0.2 for example.

Similarly, the alignment imaging apparatus 20 may be arranged to collect light reflected from the eye 150 in large NA, such as >0.1, or >0.2 for example, in order to further extend the eye alignment range, where the described alignment method is usable.

In another method, which combines the above-described eye alignment indication by using both reflection from the crystalline lens posterior surface 156 and from the surface of the cornea 126 to the same sensor, the alignment imaging apparatus 20 is arranged to collect light reflected from the eye in small NA, such as <0.07, or <0.15 for example. The small collection NA enables detection of both the reflection pattern 50B and the cornea alignment pattern 200 by using the same sensor accurately enough for producing the needed alignment information as described above. In that case, the alignment imaging apparatus 20 may have a best focus between the posterior surface 156 of crystalline lens 152 and the cornea 126 when eye 150 is at the desired working distance WD. Hence, in that case, the third target plane 110 may be between, for example approximately half-way between, the first target plane 100 and the fourth target plane 210.

Still, in an embodiment, when the first target plane 100 is arranged to approximately coincide with the posterior surface 156 of the crystalline lens 152 and when the eye 150 is close to the desired alignment, the operation of the described alignment method is independent on variations in eye alignment, eye shape, imperfections in eye surfaces or media, or eye accommodation, for example. That is because the illumination path 108 and the reception path 112 of the examination imaging apparatus 22, experience the same changes as the beams of the alignment arrangement 12 and the alignment imaging apparatus 20. Similarly, when the fourth target plane 210 is arranged to approximately coincide with the surface of the cornea 126 and when the eye 150 is close to the desired alignment, similar independency may be achieved for the cornea reflection based alignment.

FIG. 14 illustrates an example of the ophthalmic apparatus 10 where illumination and imaging arrangements are separated from each other. However, different imaging arrangement may be common. In a similar manner, different alignment arrangements may be common. Different imaging methods may utilize time division multiplexing, wavelength division multiplexing, frequency division multiplexing and/or code division multiplexing, for example. Using separate illumination and imaging may require a plurality of beam splitters 30, 30', 30".

FIG. 15 illustrates an example of the data processing unit 60 which may comprise one or more processors 500 and one or more memories 302 including computer program code. The one or more memories 502 and the computer program code may be configured to, with the one or more processors 500, cause apparatus at least to guide and/or control the user 40 to find the alignment of the ophthalmic apparatus 100 with respect to the eye 150.

FIG. 16 is a flow chart of the alignment method. In step 1500, rays of alignment light of a first alignment pattern 50 is output in a converging manner toward a first target plane 100.

In step 1502 a predetermined reflection pattern 50A of the first alignment pattern 50 is formed on said first target plane 100 based on the convergence.

In step 1504 the rays of the alignment light is caused to have an alignment light waist zone 162 that includes the first target plane 100 based on the convergence.

In step 1506 a reflection pattern 50B of the first alignment pattern 50 outside the first target plane 100 is caused to deviate from the predetermined reflection pattern 50A based on the convergence.

In step 1508, information is output on the reflection pattern 50B of the first alignment pattern 50 reflected from a posterior surface 156 of a crystalline lens 152 by a communication interface 16 of the ophthalmic apparatus 10 when the ophthalmic apparatus 10 is directed toward the eye 150 for guiding and/or controlling a user 40 based on the reflection pattern 50B of the first alignment pattern 50 that is varying with a position of said posterior surface 156 for finding the working distance from the eye 150 where the predetermined shape 50A of the first alignment pattern 50 is on said posterior surface 156.

The method shown in FIG. 16 may be implemented as a logic circuit solution or computer program. The computer program may be placed on a computer program distribution means for the distribution thereof. The computer program distribution means is readable by a data processing device, and it encodes the computer program commands, carries out method steps related to the alignment and optionally controls the processes of the alignment.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

The invention claimed is:

1. An ophthalmic apparatus, comprising:
an alignment arrangement for imaging of fundus of an eye with means for:
outputting rays of alignment light of a first alignment pattern in a converging manner toward a first target plane, forming a predetermined reflection pattern of the first alignment pattern on said first target plane based on the convergence,
causing the rays of the alignment light to have an alignment light waist zone that includes the first target plane based on the convergence, and
causing a reflection pattern of the first alignment pattern outside the first target plane to deviate from the predetermined reflection pattern based on the convergence,
wherein in order to cause the reflection pattern of the first alignment pattern to deviate from the predetermined reflection pattern outside the first target plane, the first alignment pattern has a difference in shape, structure and/or color on opposite sides of a division plane a normal of which is perpendicular to an optical axis of the alignment arrangement, or the alignment arrangement being configured to converge the alignment light differently on opposite sides of the division plane;
wherein the alignment arrangement is configured to cause the shape of the reflection pattern on one side of the first target plane to be different from the shape of the reflection pattern on the opposite side of the first target plane based on the convergence; and
wherein the ophthalmic apparatus further comprises a communication interface configured to output information on the shape of the reflection pattern of the first alignment pattern reflected from a posterior surface of the crystalline lens of the eye when the ophthalmic apparatus is directed toward the eye for guiding and/or controlling a user to select a direction of the alignment and to find the working distance from the eye where the predetermined shape of the first alignment pattern is on said posterior surface in order to align the eye and the ophthalmic apparatus with respect to each other based on the shape of the reflection pattern on said posterior surface, and for finding the working distance based on the reflection pattern of the first alignment pattern that is varying with the position of the posterior surface of the crystalline lens.

2. The apparatus of claim 1, wherein an imaging arrangement is optically configured to be in a working distance from an eye for a capture of an image of desired resolution of an interior part of the eye at least at one location in a range from the crystalline lens to fundus of the eye in response to a formation of the predetermined reflection pattern of the first alignment pattern on a posterior surface of the crystalline lens of the eye, which is an indication that the posterior surface of the crystalline lens of the eye is at the first target plane.

3. An ophthalmic apparatus, comprising:
an alignment arrangement for imaging of fundus of an eye with:
an illumination arrangement configured to direct illumination light through an illumination path toward a second target plane where the illumination light has an illumination waist, and
means for: outputting rays of alignment light of a first alignment pattern in a converging manner toward a first target plane, forming a predetermined reflection pattern of the first alignment pattern on said first target plane based on the convergence, causing the rays of the alignment light to have an alignment light waist zone that includes the first target plane based on the convergence, and causing a reflection pattern of the first alignment pattern outside the first target plane to deviate from the predetermined reflection pattern based on the convergence, an alignment imaging apparatus of an imaging arrangement, the alignment imaging apparatus being configured to capture an image of a reflection of the alignment light from the posterior surface of the crystalline lens on the first target plane;

an examination imaging apparatus of the imaging arrangement, the examination imaging apparatus being configured to receive a reflection of the illumination light from the interior part of an eye through a reception path which has a reception waist at a third plane, the illumination path and the reception path of the examination imaging apparatus being separated from each other at and between the second and third planes, which are between the first target plane and the ophthalmic apparatus; and a communication interface configured to output information on the reflection pattern of the first alignment pattern reflected from a posterior surface of the crystalline lens of the eye when the ophthalmic apparatus is directed toward the eye for guiding and/or controlling a user based on the reflection pattern of the first alignment pattern that is varying with the position of the posterior surface of the crystalline lens to find the working distance from the eye where the predetermined shape of the first alignment pattern is on said posterior surface.

4. The apparatus of claim 3, wherein:

the illumination arrangement is configured to form the illumination path with a cross sectional area smaller than a pupil of the eye at and between the second and third planes, the examination imaging apparatus is configured to form the reception path smaller than the pupil of the eye at and between the second and third planes, the imaging arrangement is configured to receive a reflection of the rays of the alignment light from a surface within an alignment range including the first target plane, the alignment arrangement being configured to form the alignment light waist region, the first target plane being within the alignment light waist region.

5. The apparatus of claim 3, wherein the alignment arrangement and the examination imaging apparatus are optically matched with each other in order to cause the examination imaging apparatus to be in the working distance from the eye in response to the formation of the predetermined shape of the first alignment pattern on the posterior surface of the crystalline lens, which indicates that the posterior surface of the crystalline lens of the eye is at the first target plane.

6. The apparatus of claim 3, wherein the illumination arrangement and the examination imaging apparatus are configured to illuminate and image the interior of an eye based on a Gullstrand's principle when the examination imaging apparatus is at the working distance from the eye.

7. An ophthalmic apparatus, comprising:

an alignment arrangement for imaging of fundus of an eye with means for:

outputting rays of alignment light of a first alignment pattern in a converging manner toward a first target plane, forming a predetermined reflection pattern of the first alignment pattern on said first target plane based on the convergence, causing the rays of the alignment light to have an alignment light waist zone that includes the first target plane based on the convergence, and causing a reflection pattern of the first alignment pattern outside the first target plane to deviate from the predetermined reflection pattern based on the convergence;

a communication interface configured to output information on the reflection pattern of the first alignment pattern reflected from a posterior surface of the crystalline lens of the eye when the ophthalmic apparatus is directed toward the eye for guiding and/or controlling a user based on the reflection pattern of the first alignment pattern that is varying with the position of the posterior surface of the crystalline lens to find the working distance from the eye where the predetermined shape of the first alignment pattern is on said posterior surface;

wherein the alignment arrangement is further configured to direct rays of light of a cornea alignment pattern in a converging manner toward a fourth target plane, the cornea alignment pattern having a difference in shape, structure and/or color on opposite sides of a division plane of the cornea alignment pattern, a normal of the division plane of the cornea alignment pattern being perpendicular to an optical axis of the alignment arrangement, or the alignment arrangement being configured to converge the alignment light of the cornea alignment pattern differently on opposite sides of the division plane of the cornea alignment pattern, form a predetermined shape of the cornea alignment pattern on said fourth target plane based on the convergence, cause the rays of the cornea alignment light to have a cornea alignment light waist zone that includes the fourth target plane based on the convergence, cause a shape of the cornea alignment pattern to deviate from the predetermined shape outside the fourth target plane, and cause the shape of the cornea alignment pattern on one side of the fourth target plane to be different from the shape of the cornea alignment pattern on the opposite side of the fourth target plane based on the convergence; and wherein the imaging arrangement is optically configured to be at a working distance from the eye for a capture of an image of an interior part of an eye at least at one location in a range from a crystalline lens to fundus of the eye in response to a formation of the predetermined shape of the cornea alignment pattern on a cornea of the eye, which indicates that the cornea of the eye is at the fourth target plane.

8. The apparatus of claim 1, wherein the communication interface comprises a user interface for a human user.

9. The apparatus of claim 1, wherein the communication interface is configured to communicate with an automatic device.

10. The apparatus of claim 1, further comprising:

one or more processors; and one or more memories including computer program code;

the one or more memories and the computer program code configured to, with the one or more processors, cause the apparatus at least to:

output information on the reflection pattern of the first alignment pattern reflected from the posterior surface of the crystalline lens through the communication interface when the ophthalmic apparatus is directed toward the eye for guiding and/or controlling the user based on the reflection pattern of the first alignment pattern that is varying with the position of said posterior surface.

11. The apparatus of claim 10, wherein the communication interface comprises a user interface for a human user, and/or the communication interface is configured to communicate with an automatic device.

* * * * *